United States Patent [19]

Flower

[11] Patent Number: 6,018,680
[45] Date of Patent: Jan. 25, 2000

[54] AWAKENABLE IONTOPHORETIC DELIVERY DEVICE FOR REDUCING ELECTRICAL SENSATION UPON APPLICATION THEREOF

[75] Inventor: Ronald J. Flower, Vernon, N.J.

[73] Assignee: Becton, Dickinson and Company, Franklin Lakes, N.J.

[21] Appl. No.: 09/173,394

[22] Filed: Oct. 15, 1998

Related U.S. Application Data

[62] Division of application No. 08/724,414, Oct. 1, 1996, Pat. No. 5,857,994.

[51] Int. Cl.[7] .................................................. A61N 1/30
[52] U.S. Cl. ........................................... 604/20; 607/120
[58] Field of Search ...................... 604/20, 114; 607/120, 607/1, 2, 3

[56] References Cited

U.S. PATENT DOCUMENTS

| | | | |
|---|---|---|---|
| 5,894,021 | 4/1999 | Okabe et al. | 604/20 X |
| 5,897,522 | 4/1999 | Nitzan | 604/20 |
| 5,908,401 | 6/1999 | Henley | 604/20 |

*Primary Examiner*—John D. Yasko
*Attorney, Agent, or Firm*—Arthur D. Dawson

[57] ABSTRACT

An iontophoretic drug delivery device includes a controller normally being in an off or low power consumption state, and a patch including electrodes, a reservoir containing an ionizable drug for transcutaneous delivery to a patient and a return reservoir. The patch is removably and electrically connectable to the controller, and delivers the drug to patient when the patch is on the patient's skin and when the controller is switched from the off or low power consumption state to an operational state. This occurs when the patch is inserted into the controller. This feature preserves the battery of the controller. Upon patch insertion, the controller periodically changes from a non-current delivery state to a current delivery state for the predetermined period of time to deliver a pulse of current to the inserted patch. A current sensor within the controller measures the current delivered to the patch. The controller switches to the non-current delivering state if the amount of current drawn is less than a predetermined amount, and is therefore off the skin, and switches to the current delivering state otherwise. This feature prevents the build up of charge on the patch electrodes and the possibility of an uncomfortable electrical sensation.

14 Claims, 6 Drawing Sheets

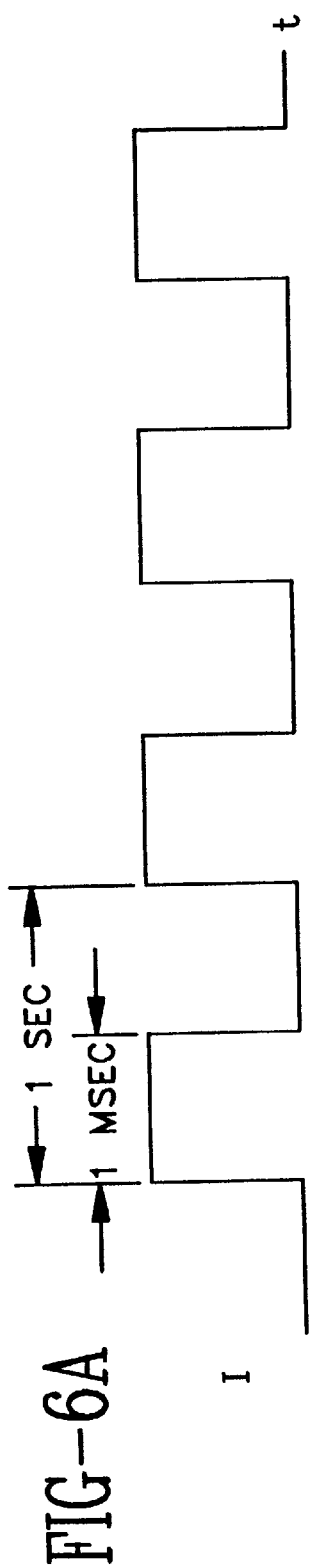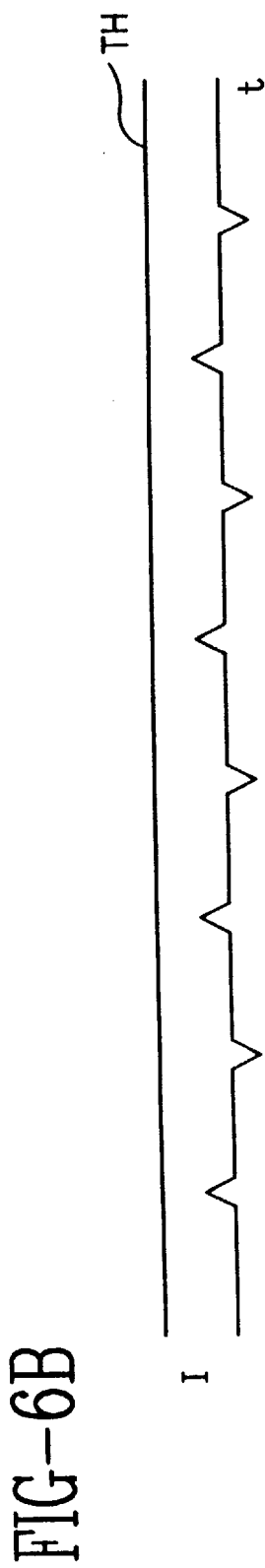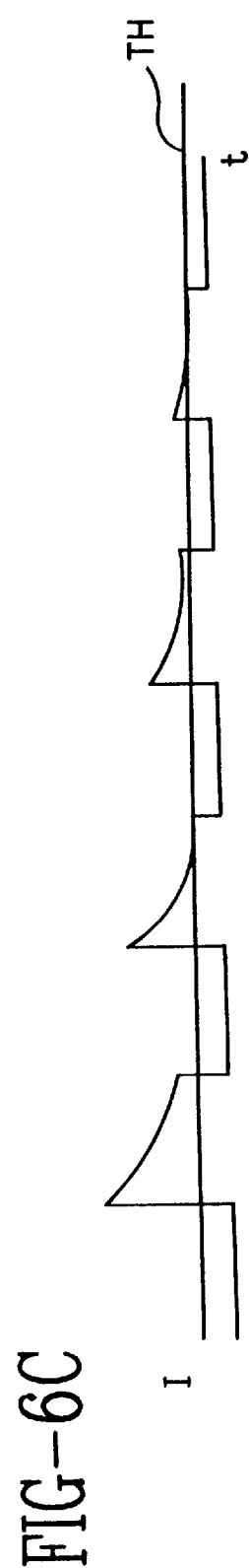

AWAKENABLE IONTOPHORETIC DELIVERY DEVICE FOR REDUCING ELECTRICAL SENSATION UPON APPLICATION THEREOF

This application is a Divisional of SN 08/724,414 filed Oct. 1, 1996 now U.S. Pat. No. 5,857,994.

BACKGROUND OF THE INVENTION

1. Field of the Invention

The invention is in the field of iontophoresis. In particular, the invention relates to awakening an electronic controller of an iontophoretic delivery device by the insertion of a drug delivery patch into the controller. The invention is also directed to a controller that prevents an electrical sensation upon the application of the drug delivery patch to the skin of a patient.

2. Description of Related Art

Iontophoresis is the migration of ions when an electrical current is passed through a solution containing ionized species, usually the ionic form of a drug or other therapeutic agent. One particularly advantageous application of iontophoresis is the non-invasive transdermal delivery of ionized drugs into a patient. This is done by applying low levels of current to a patch placed on the patient's skin, which forces the ionized drugs contained in the patch through the patient's skin and into his or her bloodstream. Passive transdermal patches, such as those used to deliver nitroglycerin for angina pectoris, estradiol for hormone replacement, and nicotine to stop smoking, can only use a limited number of drugs because they work by diffusion. Iontophoresis advantageously expands the range of drugs available for transdermal delivery, including, for example, parenteral drugs (e.g., peptides). Further, because the amount of drug delivered is proportional to the amount of current applied, the drug delivery rate can be precisely controlled by controlling the current, unlike the passive transdermal patches. This allows for more rapid delivery (onset) and drug reduction (offset) in the patient.

When compared to drug delivery by needle injection, iontophoresis has less physical and emotional trauma, pain and possibility of infection. Transdermal drug delivery by iontophoresis also avoids the risks and inconvenience of IV (intravenous) delivery. In addition, when compared to oral ingestion of drugs, drug delivery by iontophoresis puts the drug directly into the bloodstream, bypassing the GI tract, thus reducing side-effects such as drug loss, indigestion and stomach distress and eliminating the need for swallowing the drug. Iontophoresis also avoids drug loss due to hepatic first pass metabolism by the liver that occurs when drugs are ingested.

Further, transdermal drug delivery by iontophoresis permits continuous delivery of drugs with a short half life and easy termination of drug delivery. Because iontophoresis is more convenient, there is a greater likelihood of patient compliance in taking the drug. Thus, for all of the above reasons, iontophoresis offers an alternative and effective method of drug delivery, and a especially useful method for children, the bedridden and the elderly.

An iontophoretic drug delivery device typically includes a current source, such as a battery and current controller, and a patch. The patch includes an active reservoir and a return reservoir. The active reservoir contains the ionized drug, usually in a conductive gel. The return reservoir contains a saline gel and collects ions emanating from the patient's skin when the drug is being delivered into the patient's skin.

The patch also has two electrodes, each arranged inside the active and return reservoirs to be in respective contact with the drug and saline. The anode, or positive, electrode and the cathode, or negative, electrode are respectively electrically connected to the anode and cathode of the current source by electrical conductors. Either the anode electrode or the cathode electrode is placed within the drug reservoir, depending on the charge of the ionized drug. This electrode is designated as the active electrode. The other electrode is placed within the return reservoir, and is designated as the return electrode.

The active electrode has the same charge as the ionized drug to be delivered and the return electrode has a charge opposite the drug to be delivered. For example, if the drug to be delivered to the patient has a positive ionic charge, then the anode will be the active electrode and the cathode will be the return electrode. Alternatively, if the drug to be delivered has a negative ionic charge, then the active electrode will be the cathode and the return electrode will be the anode. When current from the current source is supplied to the active electrode, the drug ions migrate from the drug gel in the reservoir toward and through the skin of a patient. At the same time, oppositely-charged ions flow from the patient's skin into the saline solution of the return reservoir. Charge is transferred into the return electrode and back to the current source, completing the iontophoretic circuit.

The electronic controller between the battery and the electrodes delivers the required current to the patch. The controller may control the output current so that drug delivery is accomplished at a constant or varying rate, or over a short, long or periodic time interval. These controllers generally require relatively complex electrical circuits, sometimes including microprocessors, to meet the above requirements. Conventional manually-operated mechanical switches have been used in controllers to disconnect the battery from the controller circuitry to prevent battery drain during device storage. See, for example, the switch disclosed in U.S. Pat. No. 4,808,152 (Sibalis).

These controllers need to be switched on at the time they are placed on the body in order to begin operating. This represents a potential opportunity for error in drug delivery because the physician, nurse or patient may not remember to turn on the switch, and may also inadvertently turn off the switch before completion of the drug delivery cycle. In addition, in the case of a defective switch or a switch having poor electrical contact, there may be uncertainty concerning whether or not the device is actually delivering the therapeutic agent, or can uninterruptibly complete an entire drug delivery cycle.

Moreover, in iontophoretic delivery devices that are switched on prior to placement on a patient, electric charge has the opportunity to build up on the electrodes. A mild, but discomforting electrical sensation may be felt by the patient upon placement of the patch onto the patient's skin from the discharge of built-up electric charge. Although not painful, this is likely to reduce compliance with a drug treatment program because the patient might be afraid to use the device in the future.

In one iontophoretic device shown in U.S. Pat. No. 5,314,502 (McNichols et al.), the device, including activation circuitry and power generating circuitry, remains completely turned off until the patch is applied to the skin. At that time, the activation circuitry closes and the power generating circuitry is turned on, thereby activating the device. Because the skin acts as the switch, no conventional mechanical switch is required. Other touch-sensitive switches have been disclosed in U.S. Pat. No. 4,099,074 (Maeda et al.) and G.B. Patent 1,321,863 (Reichart). However, a problem may still exist because the device may be activated when in contact with a conductor other than a patient's skin. If the device is placed on a conductive surface, the device will be activated resulting in the unnecessary waste of the therapeutic drug, and generate uncertainty in its ability to deliver the entire drug dosage. Moreover, because the circuitry is completely turned off until the patch is applied to the skin, the device shown in McNichols et al. cannot perform self-testing prior to the application of the patch to the skin.

SUMMARY OF THE INVENTION

It is an object of the present invention to provide an iontophoretic delivery device for delivering a drug to a patient that overcome the above-described problems.

Another object of the invention is to provide a controller that is turned completely on by the insertion of a drug delivery patch into the controller.

It is still another object of the present invention to provide a iontophoretic drug delivery device which does not require the use of conventional mechanical switches or touch-sensitive switches.

In one aspect of the present invention, an iontophoretic drug delivery device is provided which includes a controller normally being in an off or low power consumption state, and a patch including electrodes, a reservoir containing an ionizable drug for transcutaneous delivery to a patient and a return reservoir. The patch is removably and electrically connectable to the controller, and delivers the drug to patient when the patch is on the patient's skin and when the controller is switched from the off or low power consumption state to an operational state. This occurs when the patch is electrically connected or inserted into the controller. This feature preserves the battery of the controller.

It is yet another object of the present invention is to provide a iontophoretic drug delivery device for preventing or reducing the potentially uncomfortable electrical sensation felt by a patient upon application of a charged patch to the skin of a patient.

In another aspect of the present invention, the controller periodically changes from a non-current delivery state to a current delivery state for the predetermined period of time to deliver a pulse of current to the inserted patch. A current sensor within the controller measures the current delivered to the patch. The controller switches to the non-current delivering state if the amount of current drawn is less than a predetermined amount, and is therefore off the skin, and switches to the current delivering state otherwise. This feature prevents the build up of charge on the patch electrodes and the possibility of an uncomfortable electrical sensation.

BRIEF DESCRIPTION OF THE DRAWINGS

These and other objects, features and advantages of the present invention can best be understood by reference to the detailed description of the preferred embodiments set forth below taken with the drawings, in which:

FIG. 6A depicts delivered current waveforms in accordance with a third embodiment of the present invention.

FIGS. 6B and 6C depict measured current waveforms in accordance with the third embodiment of the present invention.

DETAILED DESCRIPTION OF THE PREFERRED EMBODIMENTS

First Embodiment

Figure 1:
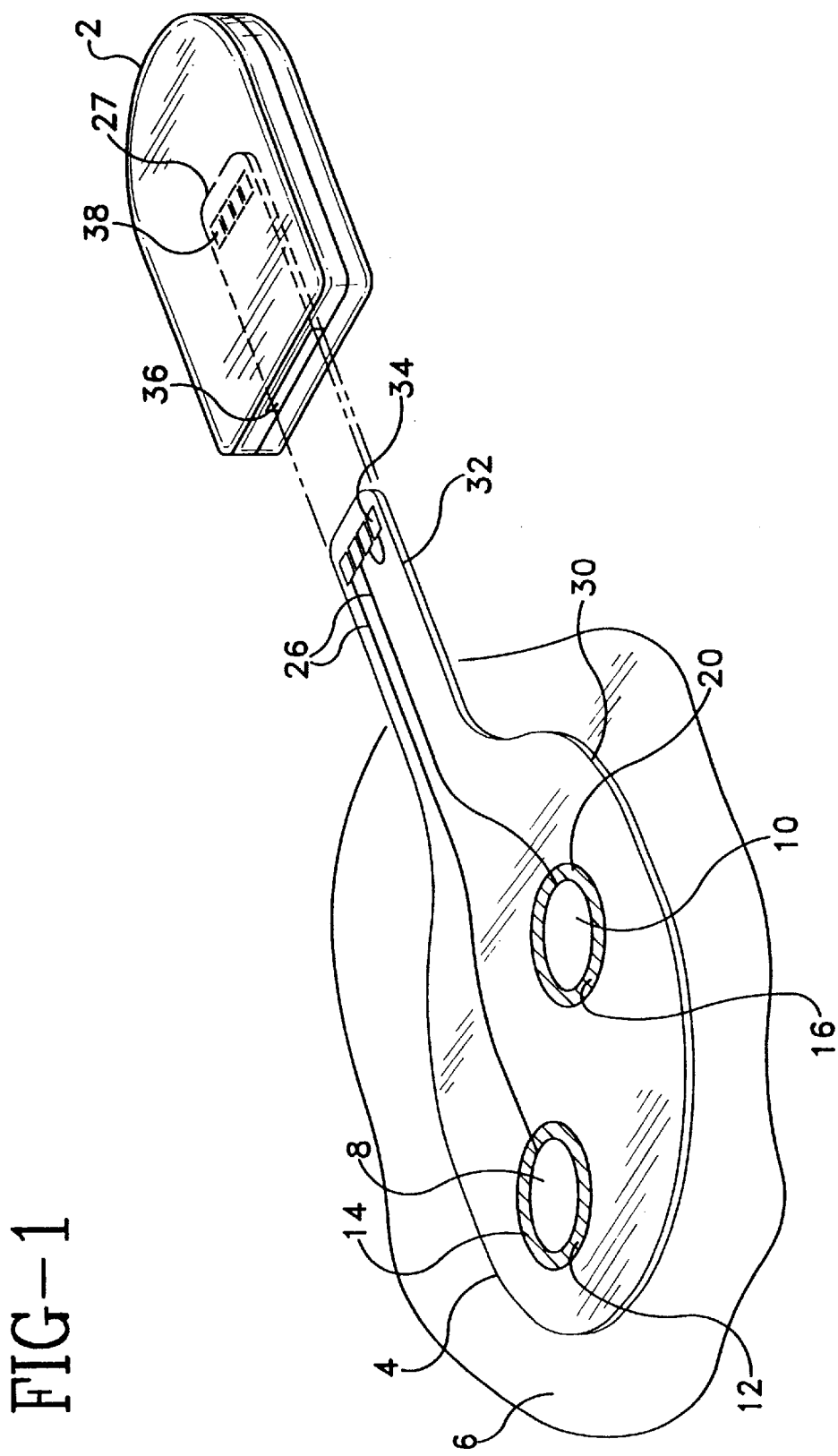
FIG. 1 is a perspective view of an iontophoretic drug delivery device in accordance with a first embodiment of the present invention.

One type of iontophoretic drug delivery device includes a separate, reusable controller 2, which can be removably and electrically connected to a patch 4 containing the drug, therapeutic agent or medicament, as shown in FIG. 1. The patch 4 is attached to the skin of the patient 6. The patch includes active electrode 8 and a return electrode 10, with the ionic drug gel 12 and active electrode 8 positioned within the active reservoir 14, and the saline or electrolyte gel 16 and return electrode 10 positioned within the return reservoir 20.

Figure 2:
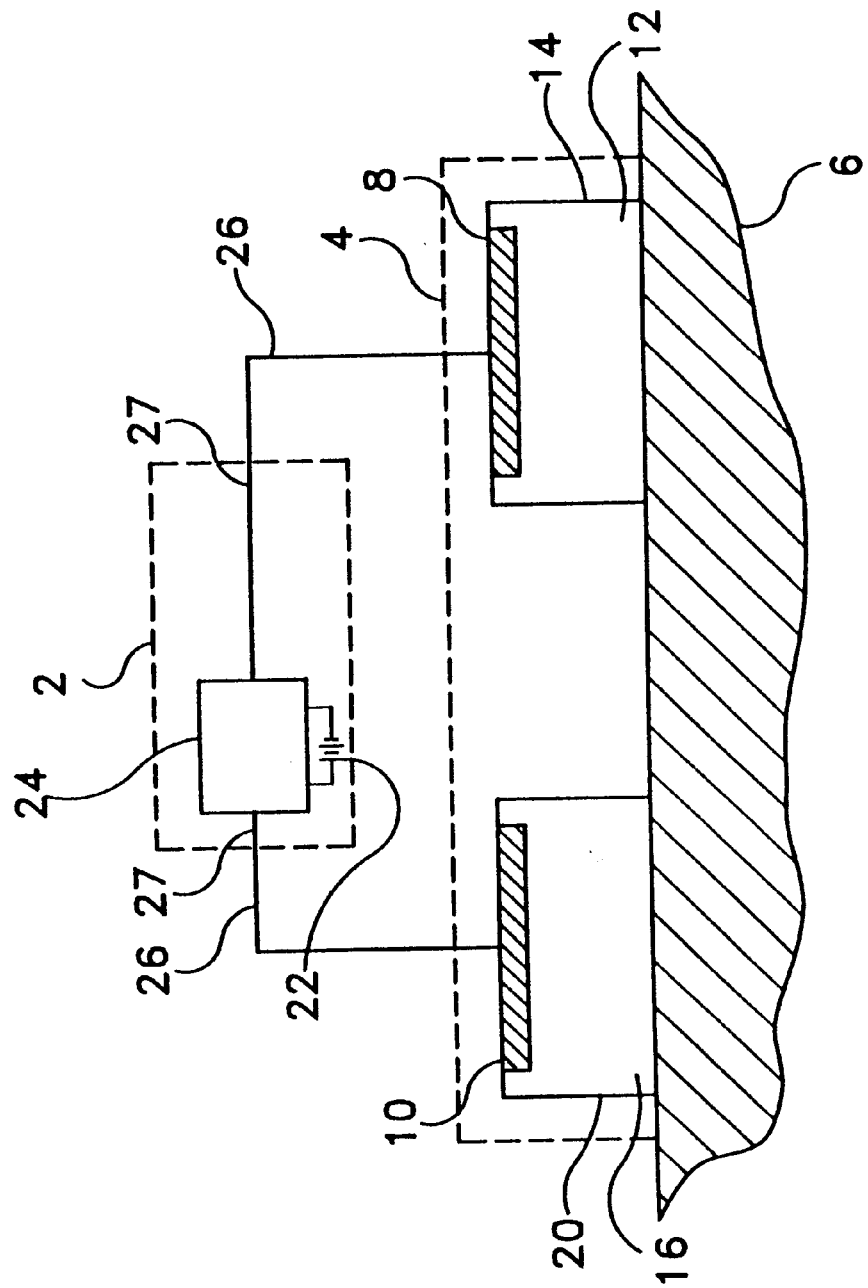
FIG. 2 shows a block diagram of a iontophoretic circuit in accordance with a second embodiment of the present invention.

The iontophoretic drug delivery device also includes a controller 2 having a power supply 22 and electronic control circuitry 24, as shown in FIG. 2. The controller is electrically coupled to the patch 4 using electronic interconnectors 26, such as a printed flexible circuit, metal foils, wires, tabs or electrically conductive adhesives. The power supply 22 in combination with the electrodes 8 and 10 and the patient's body 6 completes the circuit and generates an electric field across the body surface or skin on which the iontophoretic device is applied. The electric field causes the drug in the active reservoir 14 to be delivered into the body of the patient by iontophoresis.

Patch 4 is generally a planar flexible member formed of, for example, a biocompatible material such as woven or non-woven textiles or polymers, or any other construction well-known in the art. The patch is attached to the patient's skin using adhesives or a strap or both. The patch includes an enlarged patch body 30, which includes the active and return reservoirs.

The lower surface of the reservoirs are placed in contact with the skin, allowing the electrodes to be very close to the skin when the patch is mounted on the patient. Generally, a thin layer of the gel in the reservoirs will be between the skin and the electrodes. The electrodes are positioned so that an electrical current path is established between the electrodes 8 and 10 through the reservoirs and the patient's skin 16.

Electrodes 8 and 10 are placed in conductive contact with reservoirs 12 and 20, respectively, in a manner well-known in the iontophoretic drug delivery art. A direct current source may be connected to the electrodes 8 and 10 so that the active electrode has the same charge polarity as the ionic drug 12. When current is passed through the active electrode 8 to the return electrode 10 through the skin 16, the ionic drug 12 contained the active reservoir 14 is delivered through the skin 16 and into the patient.

Figure 4:
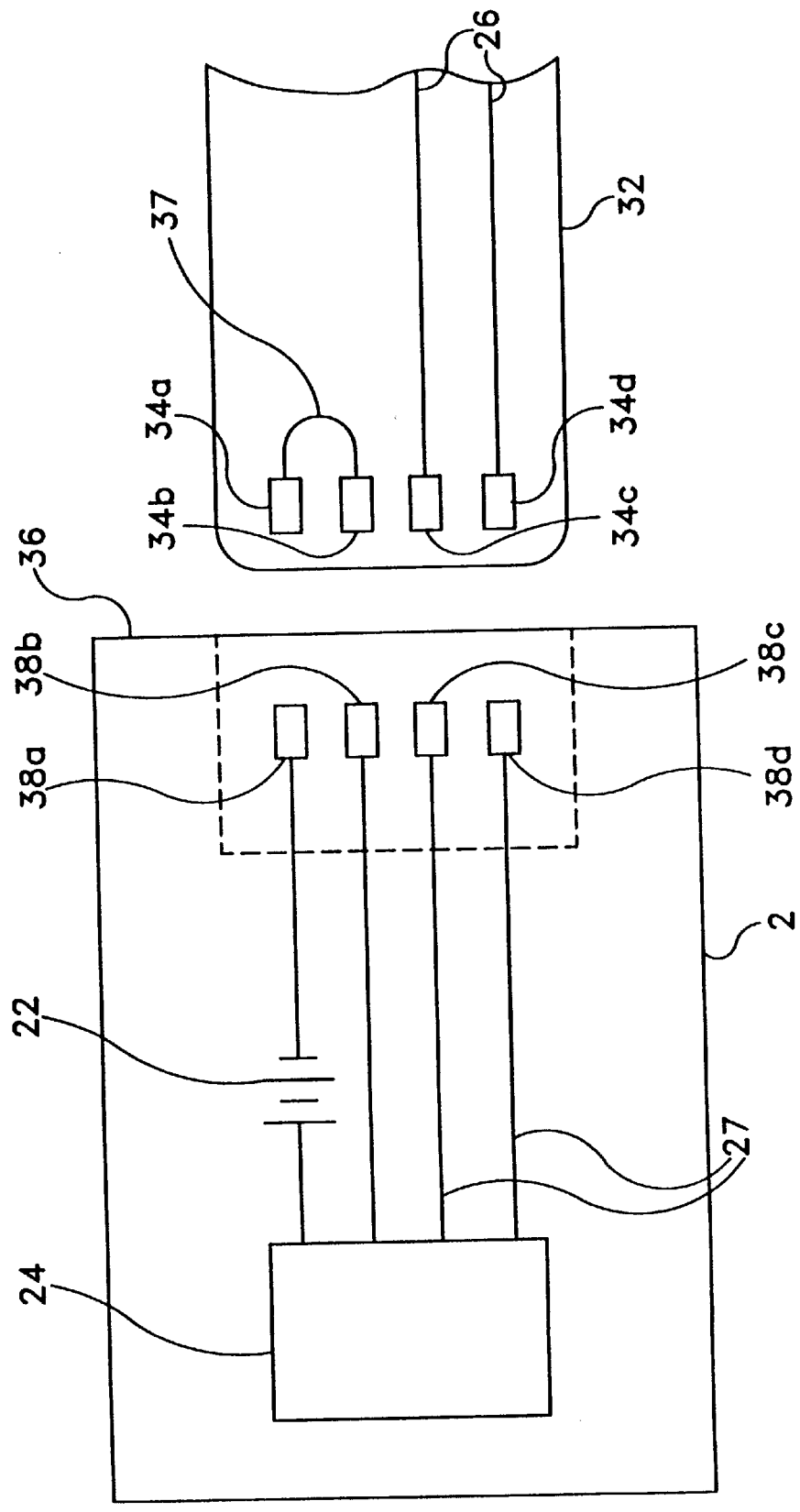
FIG. 4 shows a controller switch in accordance with the first embodiment of the present invention.

The patch also includes an extending narrow tab 32, as also shown in FIG. 4, substantially including the electrical connectors 26. The electrical connectors 26 may be one or more conductive paths extending from the electrodes 8 and 10 to exposed conductive pads 34 positioned on the marginal edge of the extended patch tab 32. The pads 34 are positioned for electrical connection with the controller when the extending patch tab 32 is inserted into the controller 2, thereby providing the electrical connection between the patch electrodes and the controller.

The controller housing 2 is generally rectangular or oval in shape, with rounded edges, and has an opening 36 in the front end to accommodate the inserted patch tab 32. The housing 2 also has a connection array 38 to which the electric circuits are electrically connected through electric conductors 27, and is preferably mounted with the electric circuits on a printed circuit board. The connection array may include plural, spaced apart electrical terminals 38a–38d to which the patch tab pads are electrically connected. Any suitable electrical interconnection device may be employed in accordance with the present invention. Further, it may be appreciated that the patch insertion and release mechanisms may take any known form, so long as the patch tab is capable of being mechanically and electrically connected to and disconnected from the controller.

Figure 3:
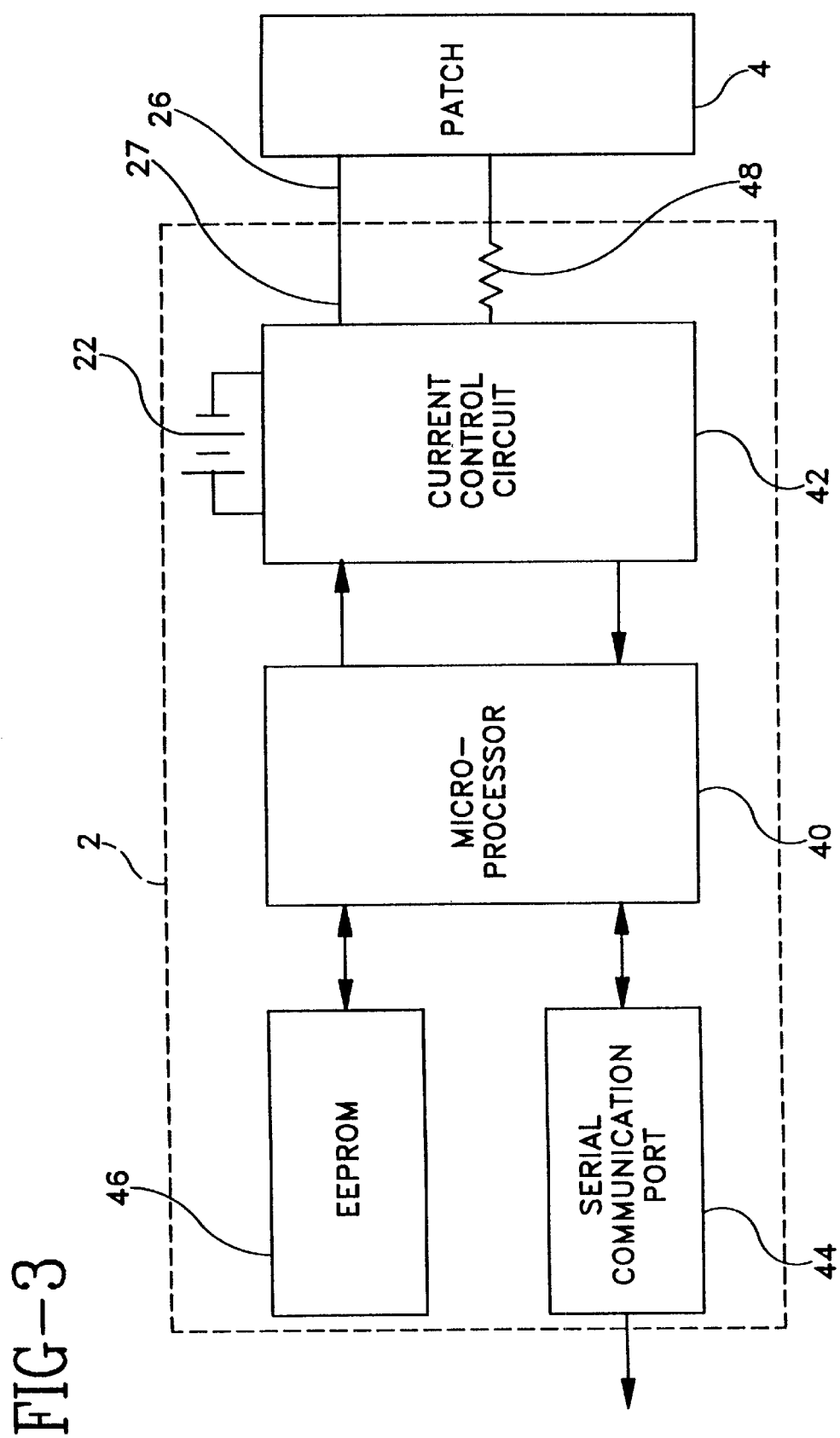
FIG. 3 shows a block diagram of a controller in accordance with a second embodiment of the present invention.

The controller 2 may include, but is not limited to, battery 22, microprocessor 40, EEPROM 46, a serial communication port 44 and current control circuit 42, as shown in FIG. 3. The microprocessor 40 provides signals to the current control circuit 42 to ensure that the required current is delivered by the current control circuit 42 to the connected patch through conductors 27 and 26 to electrodes 8 and 10 so that the correct amount of drug is delivered to the patient. The current control circuit 42 will produce from the battery 22 the required output current irrespective of the varying resistance and/or capacitance of the load (including the patient's skin, the impedance of which normally varies from patient to patient and which may change as iontophoresis takes place).

Further, voltage from a sensor, such as a current sense resistor 48, is monitored by the current control circuit 42 to ensure that the amount of delivered current is constant. The current passing through the current sense resistor 48 is the amount of current: actually being delivered through the iontophoretic patch and skin. If less or more than the required current is being delivered as indicated by the current sense resistor 48, the current control circuit 42 will adjust the current to the required level.

It would be advantageous to keep the controller circuitry completely turned off, or almost completely turned off, until the patch is inserted before device is used, so that the battery is not unnecessarily drained. In the present invention, the controller circuitry is "awakened", that is, turned fully on, not by the manual operation of a conventional mechanical switch or touch sensitive switch, but instead by the connection or insertion of the patch tab into the controller.

The controller may be kept completely turned off by (1) connecting one end of the battery 22 to one end of the controller circuitry 24, (2) connecting the other end of the battery 22 to one of the controller electrical terminals 38a, and (3) connecting the other end of the controller circuitry to another controller electrical terminal 38b, as shown in FIG. 4. Because the controller electrical terminals 38a and 38b are unconnected, the circuit is open, and the controller circuitry is completely off.

When the patch is inserted into the controller in slot 36, an electrical jumper 37 within the patch electrically connects to each of the patch tab pads 34a and 34b, and thus to each of the controller electrical terminals 38a and 38b. This closes the open circuit and thus connects the battery 22 to the controller circuitry 24. The controller circuitry, including the microprocessor, turns on and is ready to deliver current to the patch.

Second Embodiment

Alternatively, the battery may be placed within the controller circuit so that the controller circuitry always has electrical power, but is almost completely turned off. That is, only a small portion of the controller circuitry will draw current from the battery, consuming, for example, on the average, only about 10 microamperes or less. In this embodiment, because current is being drawn at all times, the battery will drain over time. But since such a small amount of current is being drawn, it will take a very long time for the battery to drain, thus ensuring a long shelf life for the controller. Since the battery is connected to the circuitry in this embodiment, self-testing prior to the application of the patch to the patient could be performed if desired.

Figure 5:
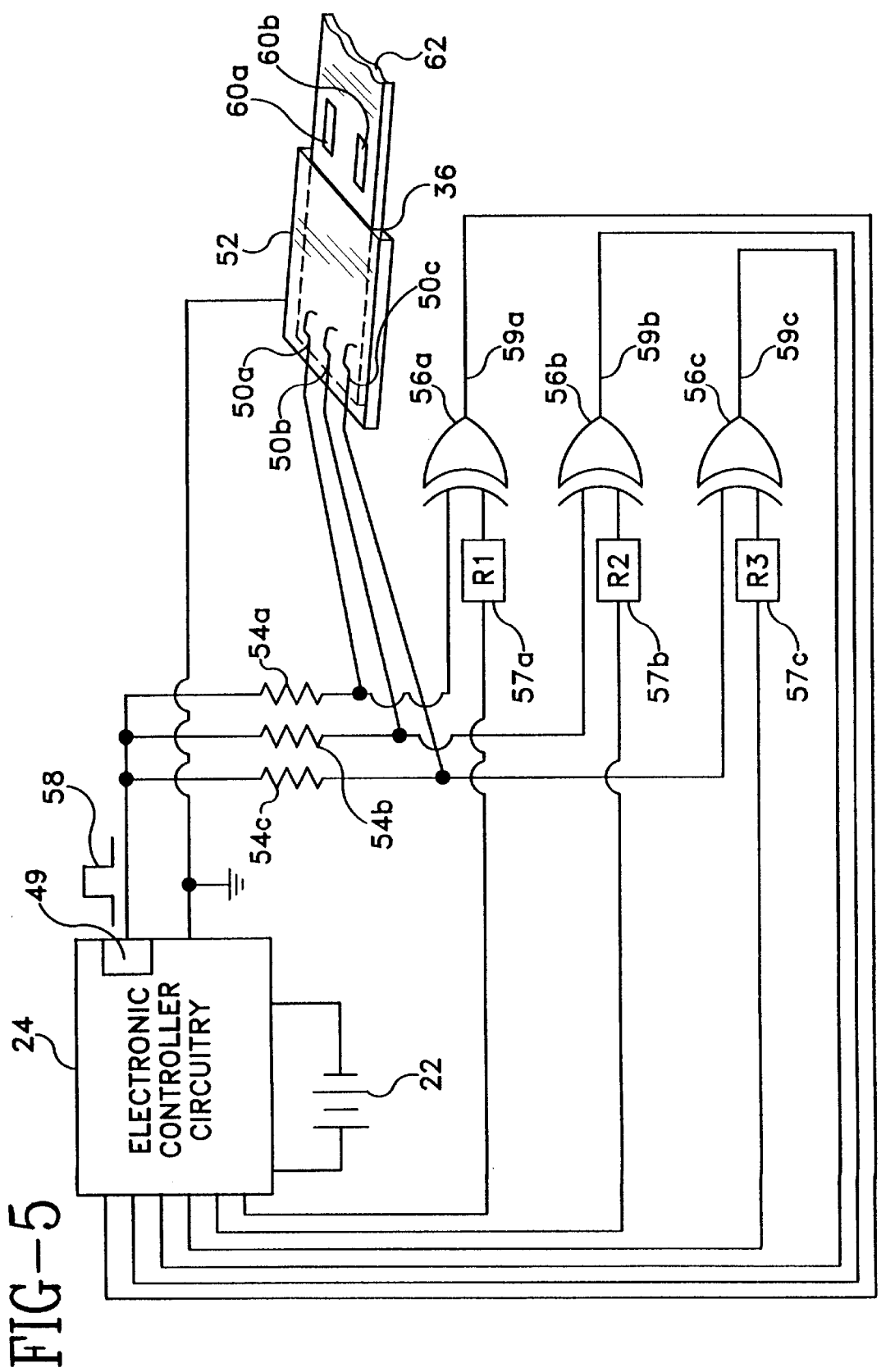
FIG. 5 shows a controller switch in accordance with the second embodiment of the present invention.

In this embodiment, the controller contains one or more normally-closed switches. For example, the switches may comprise three metal spring switches 50a, 50b and 50c normally held against a grounded metal plate 52, as shown in FIG. 5. Each switch is respectively connected to one end of a pull-up resistor 54a, 54b and 54c and to one input of a two-input exclusive OR logic circuit 56a, 56b and 56c. The other end of the resistor is connected to signal line 58 from an independent pulse generator or clock 49. The other input of the exclusive OR circuits are respectively connected to registers 57a, 57b and 57c loaded with a logic "ZERO" value by the microprocessor when the microprocessor initially turns on upon initial battery insertion (the microprocessor then turns off or goes to sleep). Because the switches 50a–50c are normally closed to ground and the inputs of the exclusive OR circuits connected to the pull-up resistors are also normally at zero voltage, the outputs 59a, 59b and 59c of the exclusive OR circuits are all logic ZERO.

The outputs 59a–59c may be combined in an "OR" circuit (not shown). The outputs 59a–59c, or the output of the "OR" circuit, serve as interrupts to turn on, or awaken, the microprocessor when any one of the outputs changes value from a logic ZERO to a logic ONE. (It will be appreciated that with known modifications the logic values "ZERO" and "ONE" may be reversed as required, and the above embodiment is not to be limited to any particular logic scheme.)

Normally, the microprocessor is asleep, and because only the independent pulse generator 49 draws energy for only a brief interval of time each period, very little current will be drawn on the average. In particular, the pulse generator 49 generates a pulse on signal line 58 periodically, for example, once a second, the pulse itself having a short duration of, for example, one microsecond to one millisecond. The pulse is sent to each of the pull-up resistors 54a–54c, which are typically each about 1 kiloohm. If any one of the spring switches 50a–50c are closed, the current flows to ground through that switch and thus no pulse is generated at the input of the respective exclusive OR circuit. Thus, if all of the spring switches are closed when the signal pulse is generated, all the outputs of the exclusive OR circuits will be at logic ZERO, and the microprocessor will remain asleep since no interrupt was generated.

In this embodiment, the patch tab 62 is designed to have openings 60a and 60b positioned so that when the patch tab 62 is slidably inserted into the controller, the openings 60 and 60b will be aligned with the area at which the switches 50a and 50b contact the metal grounding plate 52. Upon insertion into slot 36, the patch will force one or more of these normally-closed switches to remain open if there is no hole in the patch at the contact area of the switch, because the non-conducting patch tab 62 will come between the switch and the grounding plate (in this example, switch 50c will be forced open). Upon the next pulse being applied to each of the pull-up resistors 54a–54c, for the switches that remain closed through the patch openings, the input to the exclusive OR circuits will still be a logic ZERO, and there will be no change in those exclusive OR circuit outputs (in this case, outputs 59a and 59b will remain logic ZERO). Thus, those exclusive OR outputs will not cause an interrupt. However, for those switch or switches that are now open, a pulse is generated at the input of the exclusive OR circuit, causing a pulse, or a logic ONE, at the output of those exclusive OR circuits (in this case, output 59c will be a logic ONE). This pulse at the exclusive OR output will interrupt and awake the microprocessor and enter its normal operating state.

The microprocessor now examines both the exclusive OR outputs (which may be latched to preserve the logic ONE or ZERO outputs) and the positions of switches 50a–50c to confirm that a patch was actually inserted into the controller. If the microprocessor determines that the switch positions are opened or closed in accordance with the corresponding exclusive outputs 59a–59c, the microprocessor concludes that the patch was inserted and allows the controller circuitry 24 to turn on. The controller 2 is now ready to deliver current to the attached patch 4.

Otherwise, if there is a mismatch between the switch positions and the exclusive OR outputs, for example, the former are all closed while one or more of the latter are at logic ONE, the microprocessor determines that the patch was not inserted, that the interrupt was a false alarm, and returns to sleep. This could occur, for instance, if there was a brief opening and closing of one of the switches because of a jarring event, such as the controller being dropped, causing an exclusive OR output to become a logic ONE upon application of the pulse on signal line 58, thus erroneously awakening the microprocessor. In this case, the microprocessor and the controller circuitry remain turned off until an actual patch is connected.

Accordingly, in the first and second embodiments, no operation of a conventional mechanical switch is required by either medical personnel or patients; they only need to insert the patch into the controller to power up the iontophoretic device.

The second embodiment has another feature in that the microprocessor can decode the exclusive OR output circuits to determine which of the switches were opened by the inserted patch. By arranging the holes in the patch into certain patterns, various combinations of switches will be opened by the inserted patch. The switch openings are then decoded by the microprocessor to determine which patch was inserted. Accordingly, each kind of patch can be identified by the controller and this identifying information can be used by the microprocessor to determine the proper current delivery profile required for that patch.

For example, in the controller shown in FIG. 5, one of 4 types of patches can be decoded according to the opening of the switches 50a and 50b. If switches 50a and 50b are both closed, then patch type A has been inserted; if switch 50a is open but switch 50b is closed, then patch type B has been inserted; if switch 50a is closed but switch 50b is open, then patch type C has been inserted, and if both switches Soa and 50b are open, then patch type D has been inserted. Of course, it will be appreciated that any number of patch types may be accommodated, depending on the number of switches used.

Moreover, the microprocessor can monitor the switch positions or the exclusive OR outputs to determine that the patch has been removed. When the patch has been removed, the microprocessor and the controller circuitry can go asleep again until another patch is inserted and awakens them.

Third Embodiment

As explained above in the first and second embodiments, the insertion of a patch into a controller switches on the controller circuitry 24. Generally, current would now be delivered to the patch electrodes. Because the patch has not yet been applied to the skin, however, there may be a large build up of charge on the patch electrodes. The accumulated charge will quickly discharge when the patch is placed near or onto the skin, causing an uncomfortable electrical sensation.

Although not harmful or painful to any great extent, these sensations may deter future use of the device by the patient, especially if the patient is a young child. Accordingly, elimination of these sensations is greatly desired to ensure a comfortable drug delivery.

To prevent these sensations upon application of the patch to the skin, as little charge as possible should be allowed to build up on the patch. This is accomplished by keeping the powered-up controller in a non-current delivering mode until the patch is on the skin. Only at that time will the controller be allowed to deliver the required current to the patch.

The controller periodically determines whether the patch is applied to the skin. Each second, for example, a rectangular-shaped pulse of current is delivered to the patch by the controller, as shown in FIG. 6A. The pulse has a short duration, for example, between one microsecond to a few milliseconds. The current sense resistor 48 measures how much of that current pulse was actually delivered to the load, indirectly measuring the load impedance. Alternatively, a sensor may measure the voltage across the load.

As shown in FIG. 6B, if substantially no delivered current is measured, that is, the measured current is less than a predetermined threshold TH, then the load has a very high impedance, which probably means that the load is air and the patch is off the skin. The current control circuit is thus kept turned off to prevent charge from building up on the patch electrodes.

If, however, the delivered current as measured by the current sense resistor crosses the predetermined threshold, as shown in FIG. 6C, then this load has a relatively low impedance compared to that of air, meaning that the patch may be on the skin. The current control circuit can now be turned on to begin current delivery.

Because the presence of delivered current above the predetermined threshold may also result from a short-circuit, it is preferable to take additional samples to determine whether the patch is on skin or not. These samples may be longer in duration and/or occur more frequently. Moreover, if the current (or voltage) pulse measured by the current sense resistor has a time-decaying signature typical of skin, as shown in FIG. 6C, it is more likely than not that the patch is on skin, because if it was a short-circuit, the measured pulse would have substantially the same rectangular shape as the delivered pulse of FIG. 6A.

Accordingly, since the current control circuit is kept turned off most of the time, very little charge will build up on the electrodes, and the possibility of an electrical sensation being felt by the patient is greatly reduced. Moreover, even in the unlikely event that enough charge has built up on the electrodes so that: a discharge might occur, the sensation is likely to be so weak as to be unnoticeable by the patient.

Of course, it will be appreciated that the invention may take forms other than those specifically described, and the scope of the invention is to be determined solely by the following claims.

What is claimed is:

1. An iontophoretic drug delivery device comprising:
    a controller having a power source and a current generating circuit, said controller normally being in a low power consumption state;
    a patch attachable to the skin of a patient, the patch including an anode and a cathode, one of said anode and said cathode including a reservoir containing an ionizable drug for transcutaneous delivery to the patient, said patch being removably, electrically connectable to said controller, said patch for delivering drugs to the patient when said controller is in an operational state and the patch is on the skin;
    means for switching the low power consumption state to the operational state by the electrical connection of said patch to said controller.

2. An iontophoretic delivery device according to claim 5, wherein said switching means switches the low power consumption state to the operational state when said patch is inserted into said controller.

3. An iontophoretic delivery device according to claim 1, wherein said switching means comprises a normally-closed switch, one end of said switch being grounded and the other end of said switch being connected to one end of a resistor and one input of an exclusive OR circuit, the other end of said resistor being connected to a signal pulse generator, a second input of said exclusive OR circuit at a logic ZERO state, and when said switch is opened and a signal pulse from said signal pulse generator is input to said resistor, an output of said exclusive OR circuit becomes a logic ONE, causing said the low power consumption state to be switched to the operational state.

4. An iontophoretic delivery device according to claim 1, wherein said switching means comprises a plurality of normally-closed switches, one end of each said switch being grounded and the other end of each said switch being respectively connected to one end of one of a plurality of resistors and one input of one of a plurality of exclusive OR circuits, the other end of each said resistor being connected to a signal pulse generator, a second input of each said exclusive OR circuit at a logic ZERO state, and when one or more of said plurality of switches is opened and a signal pulse from said signal pulse generator is input to said plurality of resistors, one or more respective outputs of said plurality of exclusive OR circuits becomes a logic ONE.

5. An iontophoretic delivery device according to claim 4, wherein said outputs of said plurality of exclusive OR circuits are decoded to identify a type of said patch.

6. An iontophoretic delivery device according to claim 4, wherein said outputs of said plurality of exclusive OR circuits are decoded to identify a type of said patch and for causing said switching from the low power consumption state to the operational state.

7. An iontophoretic drug delivery device comprising:
    a controller having a power source, a current generating circuit and a sensor, said controller periodically delivering a pulse of current for a predetermined interval of time;
    a patch attachable to the skin of a patient, the patch including an anode and a cathode, one of said anode and said cathode including a reservoir containing an ionizable drug for transcutaneous delivery to the patient, said patch being removably and electrically connectable to said controller, said patch for delivering drugs to the patient when said controller is in a current delivering state and the patch is on the skin;
    wherein when said controller delivers a pulse of current for the predetermined period of time, said sensor measures an amount of delivered current, and based on the measured current, said controller returns to a non-current delivering state or fully switches to the current delivering state.

8. An iontophoretic delivery device according to claim 7, wherein said controller returns to the non-current delivering state if the amount of measured current is less than a predetermined threshold and fully switches to the current delivering state otherwise.

9. An iontophoretic delivery device according to claim 7, said controller further comprising a microprocessor for switching said non-current delivering and current delivering states of said controller.

10. An iontophoretic delivery device according to claim 7, wherein if the amount of measured current is greater than a predetermined threshold, one or more additional measurements of current are used to determine whether to switch fully said controller to the current delivering state.

11. An iontophoretic delivery device according to claim 10, wherein in said additional measurements of current, the period for switching between a non-current delivering state to a current delivering state is changed by said controller.

12. An iontophoretic delivery device according to claim 10, wherein in said additional measurements of current, said controller changes the predetermined time interval for changing from a non-current delivering state to a current delivering state.

13. An iontophoretic delivery device according to claim 7, wherein if the amount of measured current is greater than a predetermined threshold, the shape of the waveform of the measured current is used to determine whether to switch fully said controller to the current delivering state.

14. An iontophoretic delivery device according to claim 7, wherein said sensor instead measures a voltage delivered across the load.

* * * * *